United States Patent [19]

Howard, Jr.

[11] Patent Number: 5,621,070

[45] Date of Patent: Apr. 15, 1997

[54] ULTRA HIGH MOLECULAR WEIGHT LINEAR POLYETHYLENE PROCESSES OF MANUFACTURE

[75] Inventor: Edward G. Howard, Jr., Hockessin, Del.

[73] Assignee: E. I. Du Pont de Nemours and Company, Wilmington, Del.

[21] Appl. No.: 567,684

[22] Filed: Dec. 5, 1995

Related U.S. Application Data

[60] Continuation of Ser. No. 417,313, Apr. 5, 1995, abandoned, which is a division of Ser. No. 245,394, May 18, 1994, Pat. No. 5,478,906, which is a continuation-in-part of Ser. No. 800,868, Nov. 27, 1991, abandoned, which is a continuation-in-part of Ser. No. 500,054, Mar. 23, 1990, abandoned, which is a continuation-in-part of Ser. No. 426,916, Oct. 24, 1989, abandoned, which is a continuation-in-part of Ser. No. 288,577, Dec. 22, 1988, abandoned, which is a continuation-in-part of Ser. No. 278,913, Dec. 2, 1988, abandoned.

[51] Int. Cl.$^6$ ....................................................... C08F 6/00
[52] U.S. Cl. ........................ 528/481; 528/502 C; 528/503
[58] Field of Search ......................... 528/481, 502 C, 528/503

[56] References Cited

U.S. PATENT DOCUMENTS

| | | | |
|---|---|---|---|
| 4,246,390 | 1/1981 | Seaver | 526/352 |
| 4,587,163 | 5/1986 | Zachariades | 428/292 |
| B1 4,587,163 | 4/1990 | Zachariades | 428/292 |

OTHER PUBLICATIONS

Anagnostis E. Zachariades and J.A. Logan, The Melt Anisotropy of Ultrahigh–Molecular–Weight Polyethylene, *Journal of Polymer Science:Polymer Physics Edition*, vol. 21, pp. 821–830, 1983.

*Primary Examiner*—Thomas R. Weber

[57] ABSTRACT

Process for preparing an ultrahigh molecular weight linear polyethylene (UHMWLPE) by heating the material to above 280° C. at atmospheric pressure in an inert environment. The treated polymer is then gradually cooled in this same atmosphere.

13 Claims, 2 Drawing Sheets

ULTRA HIGH MOLECULAR WEIGHT LINEAR POLYETHYLENE PROCESSES OF MANUFACTURE

CROSS-REFERENCE TO RELATED APPLICATIONS

This is a continuation of the application Ser. No. 08/417,313, filed Apr. 5, 1995 now abandoned, which is a divisional of application Ser. No. 08/245,394, filed May 18, 1994 now U.S. Pat. No. 5,478,906 which is in turn a continuation-in-part of U.S. Ser. No. 07/800,868, filed Nov. 27, 1991 now abandoned, which is in turn a continuation-in-part of U.S. Ser. No. 07/500,054, filed Mar. 23, 1990 now abandoned, which is in turn a continuation-in-part of U.S. Ser. No. 07/426,916, filed Oct. 24, 1989 now abandoned, which is in turn a continuation-in-part of U.S. Ser. No. 07/288,577 filed Dec. 22, 1988 now abandoned, which is in turn a continuation-in-part of U.S. Ser. No. 07/278,913 filed Dec. 2, 1988 now abandoned.

BACKGROUND OF THE INVENTION

1. Field of the Invention

This invention relates to a novel ultrahigh molecular weight linear polyethylene (UHMWLPE). This novel UHMWLPE, in the form of a shaped article, exhibits in various embodiments a unique combination of properties making the material useful as a bearing surface, in general, but particularly useful as a prosthetic hip joint cup and as other prosthetic shapes for replacement of other joints of the human body.

2. Description of the Prior Art

In U.S. Pat. No. 3,944,536 (March 1976), Lupton et al. describe UHMWPE in the form of a fabricated article exhibiting an elastic modulus of 340,000 to 500,000 psi, a tensile impact strength of 140 to 600 ft lb/in$^2$, a density of 0.95 to 0.98 g/cc at 25° C., a crystalline melting point of 142° to 148° C. (as measured by differential thermal analysis) and a unique crystalline form characterized by the absence of fold spacings of 50–2000 Angstrom units (Å) and the presence of crystal spacings of about 10,000 Å. The critical feature of the process of producing this UHMWPE is disclosed to involve inducing crystallization of the molten polymer above 150° C. by rapidly increasing the applied pressure from an initial level of 1 to 1000 atmospheres to a second level of 2000 to 7000 atmospheres and then cooling rapidly while maintaining a pressure sufficient to maintain the polyethylene in the solid phase until the temperature is below the crystalline melting point of the polyethylene at atmospheric pressure.

In Kunstuffe German Plastics 77 (1987) pp. 617–622, in an article entitled "Ultrahigh Molecular Polyethylene for Replacement Joints", Eyrer et al. point out that the service life of joint replacements made of UHMWPE is limited. Analysis of the damage to over 250 explanted hip cups and tibial plateaus revealed a changed property profile which they explained by post-crystallization resulting from oxidative chain decomposition. They suggested optimizing the processing of polyethylene under higher pressure and higher temperature to increase the degree of crystallinity. The Eyrer et al. product displays a creep of above 5% at a compression of 1000 psi (6.9 N/mm$^2$) for 24 hours at 37° C.

One of the most remarkable advances in the medical field in recent years is the development of prosthetic joints, particularly the load bearing hip. The crippled and sometimes bed ridden elderly can walk again. The key to this development is UHMWPE because, not only does it have the necessary impact strength, but it initiates no adverse blood reactions. But at present, these prosthetic joints are limited to the older, less active segment of the population because the polymer tends to creep under the pressure that a younger more active person might develop while involved in recreation or employment. The creep would cause the loss of the close tolerance required between the plastic socket and the polished metal ball attached to the femur. These changes in dimensions disturb the distribution of walking forces which in turn accelerates more creep and wear. Eventually the increased pain requires a traumatic revision operation. One objective of this invention is to provide UHMWPE prosthetic joints with improved creep resistance hence removing some of the age restriction existing on the present polyethylene joints. This invention can also function in other UHMWPE-based prosthetic devices, for example, non-conforming joint assemblies such as knees which require a special balance of properties, especially with respect to tensile modulus, creep resistance, and long term dimensional stability.

SUMMARY OF THE INVENTION

This invention provides tough ultrahigh molecular weight linear polyethylene (UHMWLPE-1), and shaped articles therefrom, having a homoeomerous morphology, unusually low creep, and excellent tensile flexural properties, said polyethylene and articles being substantially free from internal stresses and having unusually long-term dimensional stability.

The invention also provides ultrahigh molecular weight linear polyethylene (UHMWLPE-2), and shaped articles therefrom, having a folded chain morphology and unusually high elongation and impact resistance.

Both polyethylenes of the invention have a molecular weight of at least 800,000, preferably at least 4,000,000, most preferably at least 6,000,000.

The homoeomerous polyethylene of the invention, UHMWLPE-1, exhibits two crystalline DSC melting points, the higher of which is greater than 144° C., said higher melting point decreasing by at least 11° C. when the polyethylene is remelted; an infrared crystallinity index of at least about 0.35, preferably at least 0.45.

UHMWLPE-1 is prepared in a novel process (Process 1) consisting essentially of the following steps:

(a) forming, by milling, casting or cold pressing and sintering or the like, an article from UHMWLPE having a molecular weight of at least 800,000, preferably at least 4,000,000, most preferably at least 6,000,000;

(b) placing the article in a pressure vessel substantially filled with a liquid that is inert to the polymer under process conditions, preferably water, heating the vessel to a temperature of at least 190° C., preferably 200°–300° C. and, after the article is molten, raising the pressure in the vessel, usually by adding more liquid, to at least 230 MPa, preferably at least 280 MPa;

(c) thereafter, cooling by reducing the temperature to about 160°–170° C. or below, preferably to 160° C. or below, most preferably to below 140° C., while maintaining a pressure of at least 230 MPa, the rate of cooling being such that temperature gradients producing internal stresses in the article are substantially avoided; and (d) cooling to a temperature below about 130° C., preferably below 100° C., and reducing the pressure to about 100 kPa, either sequentially or simultaneously, in a manner such that remelting of the article is prevented.

UHMWLPE-2 is a preferred starting polyethylene for use in Process 1 for preparing UHMWPE-1.

UHMWLPE-2 is prepared in a novel process (Process 2) consisting essentially of the following steps:

(a) forming, by milling or casting or the like, an article from UHMWLPE having a molecular weight of at least 800,000, preferably at least 4,000,000, most preferably at least 6,000,000;

(b) subjecting said article to a temperature of 280°–355° C., preferably 320°–355° C., for at least 0.5 hour, preferably at least 3 hours, in an inert atmosphere; and (c) cooling the article non-precipitously to a temperature of about 130° C. or below, the rate of cooling being such that temperature gradients producing internal stresses in the article are substantially avoided.

DETAILED DESCRIPTION OF THE INVENTION

Figure 1:
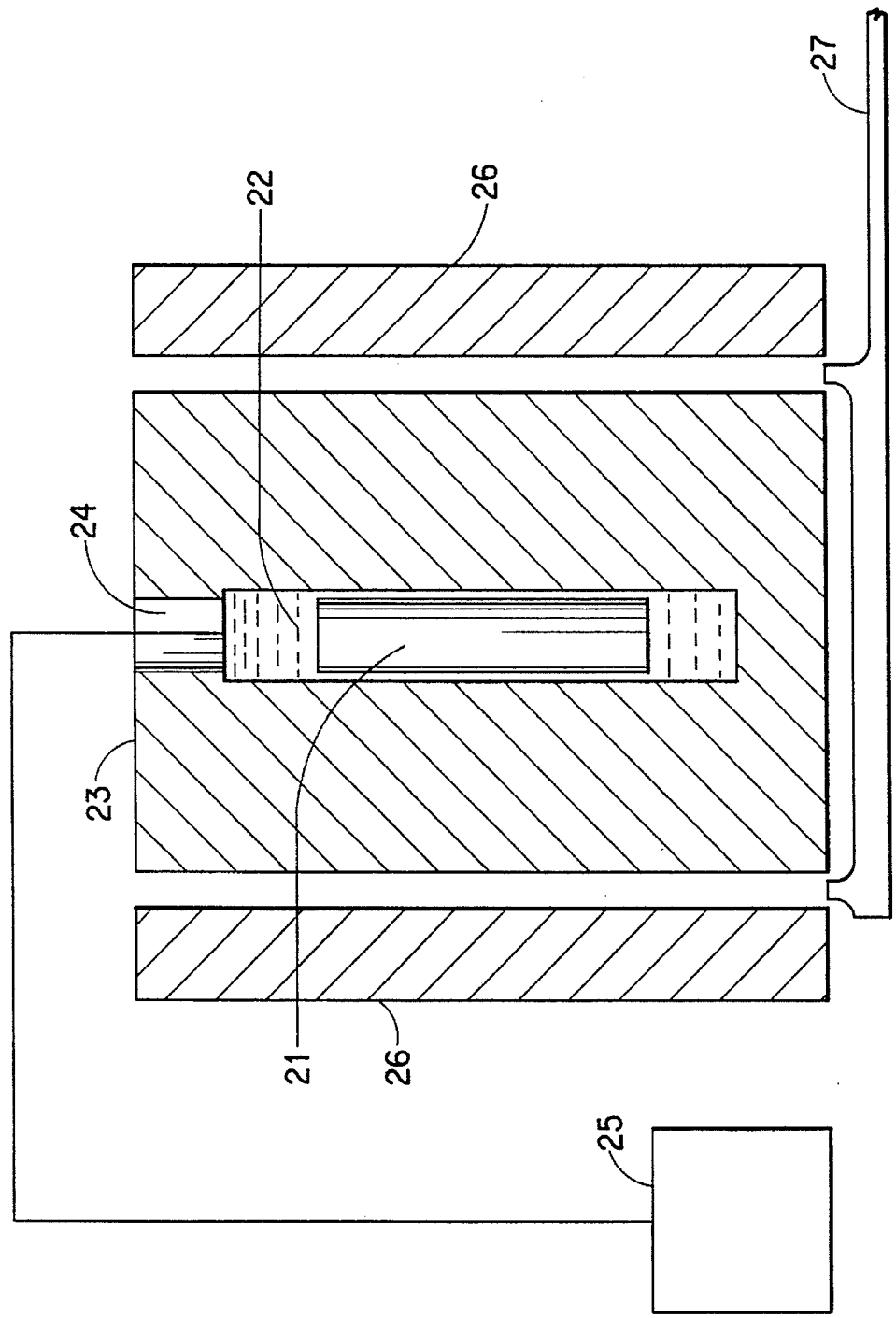
FIG. 1 illustrates an apparatus for conducting the high temperature treatment of UHMWLPE.

UHMWLPE-1 is characterized by a homoeomerous morphology comprising a bimodal distribution of crystalline molecular chain fold spacings, one group of said spacings being greater than 200 nm reflecting a population of very highly extended molecular chains, the other group being less than 50 nm. By "homoeomerous" is meant UHMW linear polyethylene which exhibits two distinct crystalline melting points corresponding to two distinct groups of crystalline molecular chain fold spacings yet which is essentially homogeneous in appearance and properties. Non-homogeneous UHMW polyethylenes of the art which may exhibit bimodal distributions of chain fold spacings and dual melting points are not homoeomerous, but rather a mixture of folded chain and partly or fully extended chain polyethylenes whose properties and appearance vary throughout the polymeric body.

UHMWLPE-1 exhibits a flexural modulus of 200–600 kpsi, a tensile stress at yield of 3.5–5.4 kpsi, a tensile stress at break of 4–9 kpsi, a tensile modulus of 250–700 kpsi, an elongation at break of 200–600%, a notched Izod impact resistance of 12–25 ft lb per in. of notch, a creep at a compression of 1 kpsi of less than 1.4% after 24 hours at a temperature of 23° C. and relative humidity of 50%.

A preferred embodiment of UHMWLPE-1, prepared by keeping the pressure in steps (b) and (c) of Process 1 over 280 MPa, exhibits compressive creep of less than 1% and a tensile modulus of at least 350 kpsi.

For certain prosthetic devices, particularly knee joints, UHMWLPE-1 having a tensile modulus in the range of 250 to about 430 kpsi is preferred. These lower modulus products are conveniently prepared by limiting the maximum pressure in steps (b) and (c) of Process 1 to between 230 MPa and 280 MPa. It is recommended, in preparing said lower modulus products at pressures between 230 MPa and less than 280 MPa, especially at pressures between 230 MPa and about 250 MPa, to use in step (a) linear polyethylene having a molecular weight of at least 4,000,000.

It has been found during the manufacture of UHMWLPE-1 products by Process 1 that use of a liquid, preferably water, in step (b) results in products having properties that are superior to those similarly processed but contained in a rigid mold made of metal or other rigid material, as describer in U.S. Pat. No. 3,944,536, even when exposed to an inert gas such a argon, as described in U.S. Pat. No. 5,037,928. Containment in a rigid mold during pressure recrystallization, in contrast to the hydrostatic method of the present invention process, results in built-in, internal stresses which adversely affect final product properties, including markedly reduced long-term dimensional stability (Example 19, Comparative Example 1).

By "internal stresses" is meant unrelieved compressive or tensile forces locked within a pressure-crystallized UHMWLPE product, said forces resulting from uneven application of pressure to an UHMWLPE article and/or significant temperature gradients within said article during its crystallization from the molten state under pressure. Such internal stresses are believed to be anisotropic and usually lead to a heterogeneous product having markedly reduced long-term dimensional stability.

A remarkable difference is found between UHMW linear polyethylene articles pressure-recrystallized by the present hydrostatic method compared to those pressure-recrystallized as in U.S. Pat. No. 5,037,928 after treatment in water a 100° C. for 4 hours; the latter expand about 10 times more than the former. Dramatic differences are also seen between hip cups of UHMWLPE processed by the present method and that of '928 after heating in air at 170° C. for 12 hours; the latter emerge yellow and grossly misshapen while the former remain white and dimensionally unchanged. Severe stress-related defects are also found in products of the art which are pressure-recrystallized under conditions wherein the material is not fully surrounded, such as in a platen press as described in U.S. Pat. No. 4,567,163; articles so processed are significantly deformed and of very limited commercial value.

It is also preferred, in step (b) of Process 1, to preheat the starting ultrahigh molecular weight polyethylene (UHMWLPE) to the required temperature of at least 190° C. outside the pressure vessel because heating UHMWLPE is very time consuming due to the high heat of fusion and low thermal conductivity of the polymer. The UHMWLPE may by heated in a dry environment, e.g., an oven, preferably in an inert atmosphere to prevent oxidation, and then transferred to the preheated pressure vessel. Because molten UHMWLPE is too viscous to flow, the article will not deform during transfer from, for instance, an oven to the pressure vessel. It has also been found that dry preheating of the polymer leads to a lower final water content in the UHMWLPE-1 product when water is used as the heat/pressure transfer medium. For example, the water content of the UHMWLPE-1 product, while dependent on the surface:volume ratio of the article formed in step (a), is usually in the range of about 0.04–0.2% by weight when the starting polymer is preheated in an oven, but in the range of about 0.7 to 2% by weight when the starting polymer is heated in water in the pressure vessel.

Further, in step (b) of Process 1, it is important to allow the starting UHMWLPE to melt completely before raising the pressure. The required heating time will depend on the thickness of the article; means of determining temperature at the center of an article, e.g., a thermocouple, is desirable for insuring that the article is molten. In repetitive operations (runs) of Process 1, it is usually sufficient to measure the article's central temperature in a first, calibration run to determine the heating time for subsequent runs.

In step (c) of Process 1, the polymer should be cooled under full process pressure until it has completely crystallized and is below the melting point of the polymer as measured at one atmosphere. Cooling rate should be sufficiently slow to avoid significant temperature gradients which produce internal stresses in the article. Preferably the cooling rate is such that a minimal difference in temperature between the pressure vessel and the polymer therein is maintained until crystallization is complete, particularly if the pressure vessel construction does not permit means for measuring the temperature of the polymer itself. For example, a cooling rate of about 10° C. per hour is desirable for a 1 inch×6 inch rod. However, although cooling rates of about 10° C. per hour are preferred, cooling rates of up to about 60° C. per hour (Example 6) have been used to provide products of this invention. Rapid cooling, as taught in the prior art, will not provide the products of this invention.

Fortunately, in the practice of steps (b)–(d) of Process 1 wherein the UHMWLPE article is immersed in a liquid within a pressure vessel, the temperature differential between the interior wall of said vessel and the polymer usually remains satisfactorily small even when the exterior of said pressure vessel is quenched with coolant. Thus, the rate of cooling of the vessel exterior is usually not critical in the practice of Process 1 for maintaining a polymer cooling rate that is sufficiently low to avoid significant temperature gradients leading to internal stresses within the polymer.

Control of cooling rate, as described above, is a particularly important feature of both Process 1 and 2 of this invention in the manufacture of larger UHMWLPE shaped articles having a smallest dimension of at least 0.2 inch, especially cross sectional dimensions of 1 inch×1–2 inches wherein avoidance of temperature gradients leading to internal stress development during cooling is more difficult yet critical to the long-term dimensional stability of the article.

In step (d) of Process 1, cooling the polymer to a temperature below its melting point at any particular pressure is necessary to ensure that none of the polymer melts as the pressure is reduced, since lowering the pressure lowers the melting point.

After step (d) of Process 1, it is optional but advisable to shave the surface of the article, i.e., remove approximately the outer 2 millimeters that might contain any liquid-affected polymer.

Products of the aforementioned process possess superior strength properties, resistance to creep under load and long-term dimensional stability, and are excellent materials for orthopedic replacement parts.

In addition to utility in the field of orthopedic replacement, the products prove useful in other applications also requiring the special properties of the products. Not only shaped articles are of interest, but also films, including oriented films, and fibers as well as other "downstream" forms and unshaped granular forms of the product will prove useful. Film formed of the product of Example 4 is exemplified in Example 12. These examples are illustrative only, and other forms, shaped and unshaped, of the present products are contemplated within the scope of the invention. Therefore, "article" shall include both shaped articles and unshaped articles.

It will be understood that the articles produced by Process 1 may be fabricated "downstream" by any of several means into other articles, care being taken to avoid remelting of the polymer.

UHMWLPE-2, a further product of the invention having a fully folded chain morphology, exhibits a flexural modulus of 150–300 kpsi; a tensile stress at yield of 3.5–4.3 kpsi; a tensile stress at break of 4–6 kpsi; a tensile modulus of 150–300 kpsi; a notched Izod impact resistance of 15–25 ft lb per inch of notch; an elongation at break of 200–1400%; a creep at compression of 1 kpsi of less than 2% after 24 hours at a temperature of 23° C. and a relative humidity of 50%; and an infrared crystallinity index of at least about 0.35. UHMWLPE-2 is prepared by heat treatment without application of pressure in Process 2 described hereinabove. In step (b) of Process 2, the polymer should be heated as close as possible to, without reaching, its decomposition temperature. In step (c) of Process 2 the hot polymer should be cooled slowly because very rapid cooling, such as immersion in cold water, causes internal voids to form. Voids result from a combination of large volume change (about 30%) on melting and poor heat conductivity in polyethylene. It is convenient to allow the polymer to cool wrapped in insulation.

The thermally treated, folded chain product, UHMWLPE-2, has improved elongation, impact resistance and crystallinity over the starting UHMW polyethylene. Preferred embodiments exhibit elongation at break of up to about 1400% (Example 10). However, UHMWLPE-2 is not equivalent in overall tensile properties and creep resistance to the pressure-recrystallized UHMWLPE-1.

As indicated hereinabove, a very important property of the UHMWLPE-1 products of this invention is creep resistance. For prosthetic devices, e.g., knee, hip, elbow joints, etc., any substantial creep can be devastating in the loss of the benefits of extremely expensive surgery. In such applications, very low creep together with high stiffness, high elongation, and high tensile strengths at yield are required. It has been found that products having these superior properties can be obtained by either using UHMWLPE-2 as the starting UHMW linear polyethylene in Process 1 or, alternatively, by inserting between steps (a) and (b) in Process 1 the atmospheric pressure heating step (b) of Process 2. Accordingly, UHMWLPE-2 is a preferred starting UHMW polyethylene for preparing UHMWLPE-1 by Process 1 for use in demanding applications such as prosthetic devices. Certain preferred embodiments of UHMWLPE-1 prepared in Process 1 wherein the maximum pressure in step (b) is at least 280 MPa and UHMWLPE-2 is used as the starting polyethylene, exhibit compressive creep of less than 1%, preferably less than 0.6%.

When UHMWLPE-2 is used as the starting polymer in Process 1, it may be introduced in either step (a) or as an article in step (b) and handled as described hereinabove for conventional starting UHMWLPE.

It is envisaged that the additional preliminary step of heating the starting UHMWLPE to 280°–355° C. will also provide superior characteristics to the product described in U.S. Pat. No. 5,037,928.

By inert atmosphere in the processes of this invention is meant a gaseous, vaporous or liquid environment that is stable and inert to process conditions. Suitable gases, vapors or liquids include water, nitrogen and the noble gases, and nonflammable, chemically inert and thermally stable liquids such as the perfluoroalkylpolyethers (Example 9). Vacuum may also be employed but is not preferred.

For purposes of this invention, ultrahigh molecular weight linear polyethylene (UHMWLPE) is defined as a linear polyethylene having an estimated weight-average molecular weight greater than about 800,000, usually 4,000,000 to 10,000,000 as defined by a melt index (ASTMD-1238) of essentially zero and a reduced specific viscosity (RSV)

greater than 8, preferably 25–30. The relationships of RSV to intrinsic viscosity and to molecular weight are those developed by R. Chaing as presented by P. S. Francis et al. in J. Polymer Science, 31, 453 (1958).

Another characteristic property of the products of this invention is their infrared crystallinity index (IRCI). This property, which fairly accurately reflects product crystallinity, is higher than in conventional UHMW polyethylene. To determine this index, samples are first obtained by microforming thin sections. Heat should be avoided during preparation of the samples. ICRI is the ratio of the band at 1894 reciprocal centimeters ($cm^{-1}$) to the band at 1305 reciprocal centimeters ($cm^{-1}$). Since the band at 1894 $cm^{-1}$ is attributed to the crystalline nature of the material and the band at 1305 $cm^{-1}$ is attributed to its amorphous nature, ICRI increases as the crystallinity increases. The product of this invention displays an IRCI of at least about 0.35, preferably at least 0.45. In fact, values of 0.73 and higher have been obtained. On the other hand, IRCI values for prior known UHMWLPE's seldom reach above 0.3.

Figure 2:
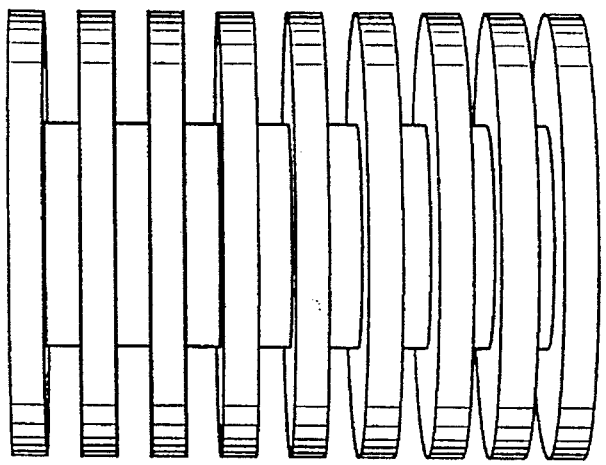
FIG. 2 shows a machined cylinder of treated UHMWLPE.
Figure 2:
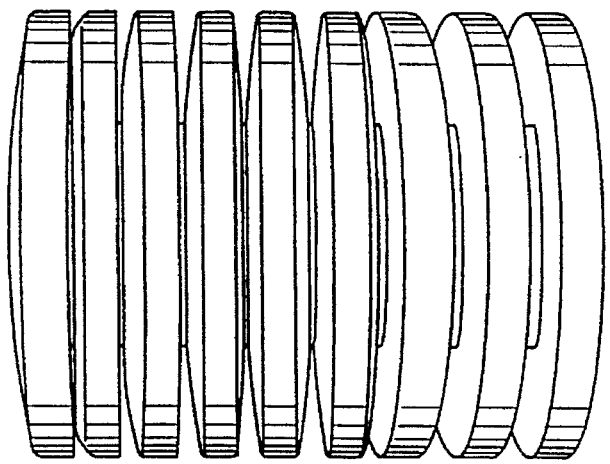

The invention will be more clearly understood by referring to the drawings and examples, which follow. In the drawings, FIG. 1 is a schematic diagram of the equipment used in the process for forming the product of the invention using the hydrostatic process. FIG. 2, shows photographically the results of a comparison of material made by U.S. Pat. No. 3,944,536, Example 2 (article "15"), and the claimed material as embodied in Example 24 (article "103").

In the examples, most of the properties are measured using standard ASTM tests.

All of the physical measurements were carried out under constant humidity (50% relative humidity) and temperature (23° C.) conditions.

Tensile modulus, ultimate tensile strength, yield strength and elongation were measured according to ASTM D-638 with the following modifications:
   samples machined into shape without lubricating liquid
   type I tensile bar
   cross head speed=0.2"/min for tensile modulus 2.0"/min for tensile stress and elongation.

Resistance to deformation (creep) was measured in accordance with ASTM D-621, where noted ASTM F-648, with the following modifications:
   samples machined into cylinders or cubes without the use of lubricating liquids
   samples measured 0.5"×0.5"×0.5"
   (ASTM F-648 only) 90 minute recovery period before measurement Flexural properties were measured according to ASTM D-790 with the following modifications:
   samples machined into shape without the use of lubricating liquids
   typical flex bar measures 0.125" thick×0.5" width×5" length
   span or gage is 2.0". (This was determined by a span/depth ratio of 16/1.)
   cross head speed=0.05"/min (calculated based on span).

Impact resistance was measured using the notched Izod test given in ASTM D-256 with the following modifications:
   samples machined into shape without the use of lubricating liquid
   type A or notched IZOD
   specimen size is 0.5"×2.5"
   0.4" from bottom of vertex to opposite side
   1.25" impacted end (from end of bar to vertex of notch)
   the notch should be the specified angle of 22.5 degrees.

The following non-limiting examples, including the improved and superior embodiments, illustrate the basic principles and unique advantages of the present invention. Various changes and modifications may be made without departing from the spirit and scope of the present invention.

EXAMPLE 1

The material used in this example is an ultrahigh molecular weight polyethylene obtained from Jet Plastics, Inc.

With reference to FIG. 1, a rod 21 measuring 6"×1⅛" was placed in the cavity 22 of a stainless steel, seamless, cylindrical pressure reactor 23. The cavity 22 had a diameter of 1.35" and was about 9" long.

Water was fed into the cavity 22 at the entry port 24 through the use of a high pressure water pump 25 powered by compressed air. Simultaneously, the reactor was heated by electrical heaters 26 surrounding the reactor.

In the first step, the rod 21 was heated to a temperature of 220° C. under a hydrostatic pressure of 200 MPa. The pressure was raised to 300 MPa while the temperature was maintained at 220° C. for 2 hours. The temperature was permitted to fall to 209° C. over another 2 hour period, and then to about 182° C. in 4 hours. Finally, the rod was cooled to 49° C. by subjecting the reactor 23 to compressed air from the blower 27 over a period of one hour and the pressure released.

The rod was removed from the reactor and the surface was shaved. The product, a sample taken substantially from the center of the rod, displayed a DSC melting point of 154.5° C., and, on reheating, a DSC melting point of 140° C.

The material, when subjected to a compression pressure of 1000 psi for 24 hours at a temperature of 23° C. and a relative humidity of 50% in accordance with ASTM D-621, deformed only 0.4%.

The other properties of the product were:
   flexural modulus—over 250 kpsi
   tensile modulus—over 300 kpsi
   tensile stress (yield)—over 3500 psi
   tensile stress (break)—over 4000 psi
   elongation (break)—less than 500%.

Its infrared crystallinity index was over 0.5.

The hydrostatic process described in this example is the best mode for preparing the product of this invention. This process has important advantages. The pressure transfer liquid, water, is non-toxic and inexpensive. The hydraulic pressure is applied equally in all directions resulting in a substantially homogeneous product. This compares to processes shown in the prior art where hydraulic pressure is applied by a piston or a ram. In these latter cases, the high shrinkage polymer tends to solidify along the heat-escaping walls making it difficult for the pistons to advance and still apply the pressure uniformly. The result is a heterogeneous product.

It should be understood that although water is the preferred liquid to use in the process, other liquids provided they are chemically inert and thermally stable under process conditions are also useful. Thus, methanol, ethanol, glycerin, glycols, etc. in addition to various aqueous solutions may be used.

The salt selected for an aqueous solution may be one that imparts a desirable property to the surface of the shaped article.

EXAMPLE 2

This experiment was carried out in a manner similar to Example 1 except that the pressure in the first step was 300 MPa. The material was maintained at 220° C. under 300 MPa for 4 hours. The temperature was allowed to fall to 190° C. over an 8-hour period. After which, it was cooled to 100° C. in 1 hour.

Samples were taken from ⅛" inside both ends of the rod and had melting points of 150.8° C. and 153.2° C. When reheated, the melting points were 135.5° C. and 138° C. respectively.

The infrared crystallinity index was 0.791; and the creep, when measured in accordance with ASTM D-621, was less than 1%. These measurements were obtained on a sample taken from the center of the rod.

EXAMPLE 3

The experiment was also carried out in a manner similar to Example 1 except for the following changes in the heating/cooling cycle:

Heat at 211° C. and 300 MPa and maintain for 1 hour;

Cool to 200° C. in 1 hour at 300 MPa;

Cool to 180° C. over 5 hours at 300 MPa (cooling rate 200°→180° C., 4°/hour); and Cool to 33° C. in 1 hour and 3 minutes.

The product from inside both ends melted at 150° C. and on reheating, at 135.5° C. The product, when tested in accordance with ASTM D-621 displayed a creep of less than 1%. Its infrared crystallinity index was 0.652.

EXAMPLE 4

A reactor with the general configuration shown in FIG. 1 having an internal diameter of 4" and being 22" long, was charged with a 3⅛"×18¹/₁₆" rod of UHMWPE (made from polymer from American Hoechst, Hostalen GUR 415). The closed vessel was evacuated, filled with water, and heated to 232° C. at which point the pressure was increased to 300 MPa with the water pump. This pressure was maintained until the end of the experiment. The reactor was held between 210° and 230° C. for 3 hours, cooled over 1 hour to 200° C., cooled to 175° C. in 5 hours (5°/hour) and then cooled to 80° C. in 7½ hours.

The resulting product rod was still in a cylindrical form with very little warpage. It measured 3⅛"×17¹⁵/₁₆". End pieces, ½" thick, were cut off each end of the rod revealing a uniform white color. Samples taken from the center of the rod on these cuts gave melting points of 152.9° C. (201 J/g). and 152.1° C. (207 J/g) when heated at 20° C./minute. When reheated, the melting points were 137.5° C.

A six inch section of the rod was sawed into ³/₁₆" thick shapes for physical tests, then carefully milled to remove saw marks to ⅛" thickness. The resulting polymer had the following properties:

| IZOD | 18.7 ft. lb./in. of notch |
|---|---|
| Flexural Modulus, | 298.9 kpsi |
| Tensile Properties | |
| Stress at yield | 4190 psi |
| Stress (at break) | 5430 psi |
| Elongation (at break) | 280% |
| Modulus | 378.3 kpsi |
| Creep (at 1000 psi load) | 0.6% |

All tests at room temperature.

The crystallinity index (IRCI) was 0.528.

Additional evidence of the products' distinctiveness is found in data produced by small angle X-ray testing. A truly characteristic small-angle X-ray scattering plot of desmeared intensity (by the method of P. W. Schmidt, Acta Cryst., 13, 480 (1960) and Acta Cryst., 19, 938 (1965)) (I×(2 theta) squared) versus scattering angle (2 theta) for the material of the invention exhibits two distinct scattering peaks associated with crystal long-spacings in the range of 480 angstroms (at 2 theta=0.184 degrees) and 4610 angstroms (at 2 theta=0.0192 degrees). The presence of the sharp diffraction peak at the lower angle is indicative of an extended polymer chain conformation (with a lamellar thickness greater than 2000 angstroms) whereas the more diffuse higher-angle peak corresponds to a lamellar thickness characteristic of conventional folded chain PE. This provides clear evidence for the presence of two scattering peaks in the subject invention material which correspond to lamellar thicknesses both above and below 2000 angstroms. By comparison, the previously patented extended chain polyethylene of Lupton et al., U.S. Pat. No. 3,944,536, was reported to exhibit a complete absence of any detectable small angle X-ray scattering in the range of 50 to 2000 angstroms. Consequently this work demonstrates that the subject invention material is morphologically distinguishable from Lupton et al.

EXAMPLE 5

In this example, the product was prepared with an exceedingly smooth surface.

A polished brass disk, about 1½" diameter, ¼" thick was pressed at 160° C. against a UHMW polyethylene plug. The combination was cooled under pressure and sealed in a heat shrinkable Teflon FEP™ tube. The polyethylene was converted in a hydrostatic system by this procedure in the vessel used in Example 4.

The heating, cooling cycle was as follows:

300 MPa and 210° C. in 1 hour;

300 MPa 210° C. to 200° C. in 1 hour;

300 MPa 200° C. to 178° C. in 6 hours, 45 minutes; and

300 MPa 178° C. to 23° C. in 2 hours, 20 minutes.

The polyethylene did shrink so that it had a smaller diameter than the disk, but the polymer stuck to the surface. When forced apart, the surface was extremely smooth.

This technique is important in preparing complicated surfaces where smoothness is extremely important, such as on bearing surfaces such as medical prosthesis for knee and hip joints, or bearings for motor shafts, etc. Machine cutting polymers always leaves very small ridges.

EXAMPLE 6

The reactor of FIG. 1, internal diameter 4" by 2" long was charged with a 3"×18" rod fabricated from American Hoescht, Hostalert GUR 415 ultrahigh molecular weight polyethylene, water, and a nominal pressure of 100 psi (690 kPa). The system was heated to 170° C. to 176° C. and held there for 1 hour, then the pressure was raised to 300 MPa. The temperature was maintained at 179° C.–174° C. for 3 hours, during which time the polyethylene crystallized. The reactor was cooled to 79° C. in 1.7 hours (approximately 60° C. per hour).

Two samples were taken; one from the center of the rod and another ½ inch from the outer surface of the rod. The melting points, as measured by DSC; were 150.9° C. and 150.4° C., respectively, and upon reheating, 136.6° C. and 137.3° C. Thus, the increases in melting points were 14.3° C. and 12.7° C., respectively. The infrared crystallinity index was 0.5.

EXAMPLE 7

This example shows that the polymer can be cooled at a rate as high as 34.5° C. per hour in the critical cooling step (step 5) if proper precautions are taken to limit temperature gradients.

A one inch rod of UHMWLPE from Jet Plastics, Inc. was used. It was placed in the pressure vessel with water and subjected to the following treatments:

300 MPa and 220° C. for 2 hours;
300 MPa, cool to 200° C. in 50 minutes;
300 MPa, cool to 177° C. in 40 minutes;
300 MPa, cool to 35° C. in one hour.

A test sample taken one-half inch from the end of the rod and in the center displayed a DSC melting point of 153.8° C., and, on reheating a DSC melting point of 139.7° C.

The material, when subjected to a compression pressure of 1000 psi for 24 hours at 23° C. and a relative humidity of 50% in accordance with ASTM D-621 deformed 0.5%.

EXAMPLE 8

Superior Enhanced UHMW Polyethylene prepared by Preheating Polymer to 325° C.

A 3 1/16"×15" rod of UHMW polyethylene (Hoechst GUR415, fabricated by PolyHi) was heated to 325° C. in an atmosphere of $N_2$ for six hours. The hot rod was quickly placed in a pressure vessel preheated to 212° C. The vessel was sealed immediately and pressured with water to 300 MPa. The cooling schedule was as follows:

212° to 191° C. 65 minutes
191° to 181° C. 63 minutes
181° to 175° C. 2 hours
175° to 174° C. 6 hours, 26 minutes
174° to 45° C. 3 hours, 15 minutes The rod was cut into test samples and analyzed with the following results:

| DSC (Differential Scanning Calorimetry) | | |
|---|---|---|
| | Center of Bar | 1 cm from Bar Edge |
| m.p., °C. | | |
| 1st heat | 150.5 | 152.4 |
| 2nd heat | 137.9 | 139.0 |
| ΔT | 12.6 | 13.4 |
| Heat of Fusion | | |
| 1st heat | | 198.8 J/g |
| 2nd heat | | 134.4 J/g |
| Infrared Crystallinity Index | | |
| (Samples cut from within 5 mm of bar edge) | | |
| In Bar Direction | | 0.613 |
| Perpendicular to Bar Direction | | 0.633 |
| Flex Modulus, (kpsi) | | 424.0 |
| | | 386.1 |
| Deformation (Creep) (% at 1000 psi load) | | |
| In Bar Direction | | 0.4 |
| Perpendicular to Bar Direction | | 0.6 |

| Density g/ml | | |
|---|---|---|
| Gradient column | | 0.9595 |
| Infra Red | | 0.957, 0.958 |

| Tensile Properties: | In Bar Direction (6" Test Bars) (Type I) | Perpendicular to Bar Direction (2 ½" Test Bars) (Type V) |
|---|---|---|
| Stress, psi | | |
| Yield: | 4743 | 4516 |
| | 4758 | 4526 |
| Max: | 4743 | 5614 |
| | 4758 | 5005 |
| Break: | 4396 | 5004 |
| | 3695 | 5040 |
| Modulus, kpsi | 611.1 | 520.3 |
| | 613.0 | 513.9 |
| Elongation, % at break | 355 | 433 |
| | 315 | 400 |

| IZOD IMPACT, ft. lb. /in. of notch | |
|---|---|
| Bar Direction | Perpendicular to Bar Direction |
| 24.8 | 26.1 |
| 22.0 | 25.0 |

EXAMPLE 9

Effect of Sequence of Heat-treatment, Cooling, Reheating to a Lower Temperature, and Pressure Recrystallization on UHMWPE.

A UHMW PE bar (3"×15") was heated for five hours at 325° C. under $N_2$, then slowly cooled to room temperature. It was reheated to 225° C., and pressure recrystallized as described in Example 8 according to the following schedule:

| | | |
|---|---|---|
| 241° to 191° C. | 300 MPa | 2 hours, 15 minutes |
| 191° to 181° C. | 300 MPa | 2 hours |
| 181° to 171° C. | 300 MPa | 6 hours |

The resulting product was machined into test pieces and analyzed with the following results:

| DSC | | |
|---|---|---|
| | Center of Bar | 1 cm in from Bar Edge |
| m.p., °C. | | |
| 1st heat | 149.3 | 149.1 |
| 2nd heat | 134.3 | 135.2 |
| ΔT | 15 | 13.9 |
| Heat of Fusion | | |
| 1st heat | 223.6 J/g | 229.6 J/g |
| 2nd heat | 156.1 J/g | 162.3 J/g |
| Infrared Crystallinity Index | | |
| In Bar Direction | | 0.745 |
| Perpendicular to Bar Direction | | 0.759 |
| Tensile Properties | | |
| Stress, psi | | |
| At Yield | 4706 | 4463 |
| At Break | 5362 | 5326 |
| Modulus, kpsi | 649.7 | 404.2 |

| Elongation, % | | |
|---|---|---|
| At Yield | 4.7 | 4.5 |
| At Break | 330 | 335 |
| Deformation (Creep) | 0.4 | |
| (% at 1000 psi load) | 0.3 | |

Effect of Preheating

The preliminary heating of this example may be achieved in an atmosphere of refluxing vapors instead of $N_2$, as described below.

A 3"×18" rod of UHMWLPE (American Hoechst, Hostalen GUR 415) was heated in refluxing vapors of Krytox®-143AZ (E. I. du Pont de Nemours and Company, Wilmington, Del.) (at 333°–335° C.) for 2 hours, 40 minutes. Krytox®-143AZ is a perfluoroalkylpolyether that is a nonflammable, chemically inert liquid having unusually high thermal and oxidative stability. Vapors of other liquids demonstrating these characteristics may also be suitable. The overall system was wrapped with glass insulation to facilitate slow cooling and protected by a nitrogen atmosphere. As compared to the starting material, the resulting product has improved crystallinity (IRCI 0.47 versus 0.27), a tensile modulus (300 kpsi versus 210), and tensile strength at yield (3850 psi versus 3400). Most significantly, the product displays a large increase in elongation at break (893% versus 315%).

When the above described material was recrystallized from 220° C. under 300 MPa, a new polyethylene resulted possessing extremely high elongation at break (667%) along with the high tensile strength at yield (4900 psi) and the tensile modulus (574 kpsi) expected of the superior, enhanced UHMWLPE materials.

| Flex Modulus, kpsi | 436.4 | |
|---|---|---|
| | 431.2 | |
| | 433.80 | (av) |
| Density | .9684 | |
| IZOD IMPACT, | 17.1 | |
| (ft. lb./in. of notch) | 15.9 | |
| | 16.5 | (av) |

EXAMPLE 10

Effect of Heating Temperature on UHMW PE

Cubes (¾") of UHMW polyethylene (Hoechst Hostalen GUR 415, m.w. 4–6 million, fabricated by Westlake) were wrapped in Teflon® film and placed in a large test tube protected from air with $N_2$. A small thermocouple was inserted into the center of one of the cubes to determine the time necessary for the samples to reach test temperature. A plug of glass wool was placed above the sample to control convection currents. The tube was heated with a Wood's metal bath. After the heat treatment was complete, the samples were wrapped in insulation to ensure slow cooling. At a bath temperature of 250° C., the samples required 45 minutes to reach test temperature.

| Time Sample at Temperature hrs:min | Test Temperature °C. | Crystallinity Index (by IR) |
|---|---|---|
| 4:00 | 250 | 0.232 |
| 20:00 | 250 | 0.244 |
| 4:00 | 293 | 0.264 |
| :01 | 293 | 0.230 |
| 4:00* | 320–325 | 0.374 |
| 1:00* | 334–335 | 0.378 |
| 1:00* | 340–342 | 0.391 |

*Heated by submerging sample wrapped in Teflon® film under Woods metal as described in the following paragraph.

Effect of Time on Heating UHMW PE

Small cubes (¾") of UHMW PE cut from the rod form of Hoechst Hostalen GUR 415 were wrapped in Teflon® film, tied to a glass rod, and pushed under the surface of a Wood's metal bath. A small thermocouple was inserted in one of the cubes; when plunged into a 322°–329° C. bath, twelve minutes were required for the sample center to reach 321° C. The time at temperature (not the time in the bath) is recorded below. The samples were removed from the bath and wrapped in glass fiber insulation to permit slow cooling which required 1.5 hours to reach 80° C. The extent of change was determined by measuring crystallinity indices.

| Time Sample at 320–325° C. (hrs:min) | Crystallinity Index by (IR) |
|---|---|
| no heating | .258 |
| 0:10 | .261 |
| 0:20 | .294 |
| 1:00 | .330 |
| 4:00 | .374 |

Heat Treatment of UHMW PE (Large Scale)

A 3" diameter by 18" bar of UHMW polyethylene (Hoechst Hostalen GUR 415, m.w. 4–6 million, fabrication by Westlake) was heated under nitrogen at 325° C. for 4 hours (65B). The bar was cut into test pieces as was a bar of the same starting polymer that had not been treated. Tests were run sequentially:

| | Untreated Polymer | | Thermally Treated sharper (narrow curve) | | % Difference |
|---|---|---|---|---|---|
| DSC | | | | | |
| m.p. °C. | 139.7 | | 137.5 | | |
| Heat of Fusion J/g | 154.6 | | 197.5 | | +28 |
| Crystallinity Index (IR) | 0.258 | | 0.386 | | +50 |
| Tensile Properties | | | | | |
| Stress, psi | | | | | |
| Yield | 3380 | | 3694 | | |
| | 3456 | | 3642 | | |
| | 3418 | (av) | 3668 | (av) | +7.3 |
| Max. | 5361 | | 4706 | | |
| | 4864 | | 4673 | | |
| | 5113 | (av) | 4690 | (av) | |
| Break | 5361 | | 4705 | | |
| | 4864 | | 4673 | | |
| | 5113 | (av) | 4689 | (av) | |
| Elongation, % Break | 330 | | 490 | | |
| | 300 | | 500 | | |

15
-continued

|  | Untreated Polymer | | Thermally Treated sharper (narrow curve) | | % Difference |
|---|---|---|---|---|---|
| Modulus, kpsi | 315 208.4 210.5 209.5 | (av) (av) | 495 244.6 253.7 249.1 | (av) (av) | +57 +19 |
| Flex Modulus, kpsi | 124.4 137.1 130.7 | (av) | 151.5 146.8 149.1 | (av) | +14 |
| IZOD IMPACT, (ft. lb./in. of notch) | 15.93 20.81 18.37 | (av) | 19.97 22.68 21.32 | (av) | +16 |
| Deformation (Creep) (% at 1000 psi load) | 1.8 1.7 | | 1.6 1.3 | | −17 |

Similarly, a 3" diameter bar of different UHMW polyethylene (Himont 1900, m.w. 1,000,000) was heat pretreated in an inert atmosphere, for example, of $N_2$. The product had greatly improved elongation and impact resistance.

|  | Untreated Polymer | | Thermally Treated | | % Difference |
|---|---|---|---|---|---|
| DSC |  |  |  |  |  |
| Heat of Fusion J/g | 166.3 | | 190.7 | | +15 |
| Crystallinity Index (IR) | .284 | | .379 | | +33 |
| Tensile Properties |  |  |  |  |  |
| Stress, psi |  |  |  |  |  |
| Yield | 3544 3703 3622 | (av) | 3721 3589 3655 | (av) | −0 |
| Max. | 7387 7190 7289 | (av) | 6545 5999 6272 | (av) | −14 |
| Elongation, %, Break | 200 216 208 | (av) | 343 293 318 | (av) | +53 |
| Elongation, %, Yield | 16.6 20 | | 20 16.6 | | |
| Modulus, kpsi | 128.4 216.2 202.7 | (av) | 212.7 192.7 202.7 | (av) | 0 |
| IZOD Impact, (ft. lb./in. of notch) | 13.05 11.94 12.49 | (av) | 24.26 17.12 21.09 | (av) | +65 |

Effect of 4 Hour Heating at Higher Temperatures

Sample bars (18"×3" diameter) of UHMWPE (Hoechst Hostalen GUR 415, fabricated by Westlake) were heated in an oven under nitrogen for 4 hours at the temperatures shown below, then cooled to room temperature and tested.

| Temp. °C. | Crysty. Index | IZOD ftlb/in of notch | Yield psi | TENSILE PROPERTIES Modulus kpsi | Elong(b) % |
|---|---|---|---|---|---|
| as is | 0.26 | 18.4 | 3400 | 210 | 315 |
| 325 | 0.386 | 22.7 | 3700 | 250 | 495 |
| 334 | 0.47 | 21.8 | 3900 | 300 | 893 |
| 342 | 0.514 | 20.7 | 4100 | 240 | 1100 |
| 349 | 0.570 | 16.8 | 4200 | 250 | 1335 |
| 355 | 0.602 | 2.1 | 4200 | 280 | 1630 |

The results show a startling improvement in properties following a 4 hour heat treatment at temperatures above 320° C.

EXAMPLE 11

A 3" diameter bar (rod), 18" in length, of American Hoechst Hostalen GUR 415 ultrahigh molecular weight polyethylene, was heated in an oven and then encapsulated with low molecular weight polyethylene by rolling the hot rod onto a 1/16" sheet of low molecular weight polyethylene heated to 180° C. on a large hot plate. An intervening sheet of "Teflon" Polytetrafluoroethylene film was kept on the encapsulated rod to prevent sticking to the hot plate. The rod ends were similarly sealed. The "Teflon" film was kept on the encapsulated rod to prevent sticking in the reactor.

The bar was heated to 225° C. under a nitrogen atmosphere and transferred to the reactor at 225° C. After sealing, the reactor pressure was taken to 300 MPa which caused the temperature to reach 237° C. The reactor was permitted to cool to 180° C. in 6.5 h, then maintained at this temperature for 1 h. The temperature was dropped to 170° C. held at this temperature for 3 h, then cooled slowly to 150° C. from where it was cooled rapidly.

The rod, which remained coated, was cut and machined into two test pieces (A and B) which gave the following results:

|  | SAMPLE | |
|---|---|---|
| DSC | A | B |
| 1st Heat: |  |  |
| Melt point, °C. | 149.1 | 153.7 |
| Heat of Fusion, J/g | 219.8 | 209.5 |
| 2nd Heat: |  |  |
| Melt point, °C. | 135.5 | 136.6 |
| Heat of Fusion, J/g | 141.2 | 144.9 |
| Crystallinity Index (IR) | 0.566 | 0.567 |
| Tensile Properties: |  |  |
| Stress, psi |  |  |
| At Yield | 4149 | 4076 |
| At Max. | 7448 | 8138 |
| At Break | 7448 | 8138 |
| Elongation, % | 323 | 34  6 |
| Modulus, kpsi | 363.6 | 358.2 |
| Creep, % | 0.6 | 0.6 |
| IZOD Impact, (ftlb/in. of notch) | 15.9 | 15.8 |

EXAMPLE 12

A 5.75" segment of enhanced ultrahigh molecular weight polyethylene prepared as in Example 4, was skived to two films (A and B), of 11 mil and 5 mil thickness, respectively. The following properties were obtained (averaged from five tests per film sample):

|  | SAMPLE | |
|---|---|---|
| Tensile Properties: | A | B |
| Stress, psi | | |
| At Yield | 3035 | 3108 |
| At Max. | 6554 | 4083 |
| At Break | 6481 | 4083 |
| At 5% Elongation | 2667 | 2705 |
| Modulus, kpsi | 129.7 | 165.6 |
| Elongation at Break, % | 470 | 237.6 |

The skived films were hot drawn in a tenter frame at 140° C. One piece of the 5 mil film was drawn 6 fold in one direction (C). A second piece of the 5 mil film was drawn 3 fold in both directions (D):

|  | SAMPLE | |
|---|---|---|
|  | C | D |
| Tensile Stress, psi | | |
| At Yield | 37,819 | 13,720 |
| At Max. | 42,058 | 19,358 |
| At Break | 46,426 | 18,995 |
| Tensile Modulus, kpsi | 93.3 | 94.9 |
| Elongation at Break, % | 56 | 132.4 |
| Thickness, mils | 2.6 | 1.6 |

EXAMPLE 13

Two bars (18"×3" diameter) of UHMWPE (Hoechst Hostalen GUR 415, fabricated by Westlake) were heat-treated in a forced $N_2$ oven at 335° C. to 345° C. for 4 hours. The oven was slowly cooled to room temperature.

One bar was placed in a pressure vessel and heated at 220° C. for 2 hours before being pressured to 300 MPa with water as pressure transfer liquid. The temperature was allowed to cool to 185° C. for 2 hours, allowed to cool to 174° C., held for 2 hours at this temperature, cooled over 5 hours to 150° C., then cooled rapidly to 90° C. All cooling was carried out under 300 MPa pressure.

Test pieces were cut from both bars and tested with the following results:

|  | Heat Only | Heat, Pressure Recryst. |
|---|---|---|
| DSC | | |
| M.P. °C. | | |
| 1st heat | 139.7 | 147.9 |
| 2nd heat | 134.7 | 136.1 |
| Heat of Fusion, J/g | | |
| 1st heat | 211.2 | 245.8 |
| 2nd heat | 182.5 | 188.8 |
| Tensile Properties | | |
| Stress, psi | | |
| Yield | 3930 | 4778 |
| Max | 6023 | 5117 |
| Break | 5779 | 5102 |
| Modulus, kpsi | | 415.2 |
| Elongation, % | | |
| Yield | 18 | 7 |
| Break | 920 | 532 |
| IZOD Impact ftlb/in of notch | 22.6 | 22.2 |
| Crystallinity Index | 0.446 | 0.812 |

EXAMPLE 14

A reactor with a configuration similar to that shown in FIG. 1 having an internal diameter of 5" and a length of approximately 70" was charged with a 4"×60" rod of Hoechst Hostalen GUR 415 UHMWPE manufactured by Poly Hi, Inc. The closed vessel was evacuated, filled with water, and heated to 250° C. over a period of 1.5 h. This temperature was maintained for an additional 2 h to insure that the UHMWPE rod was heated uniformly and no significant temperature gradients were present. The pressure was then raised to 35,000 psi (241 MPa). This pressure was maintained for the duration of the experiment. After 1 h, the temperature was ramped down to 175° C. over a period of 3 h (cooling rate approximately 25° C./h). The temperature of 175° C. was maintained for 1 h, and the reactor was then cooled to 75° C. over a period of 2 h. The pressure was then released, and the rod was removed from the autoclave.

A 12" length was cut from the rod for evaluation. A sample from the center of-the rod was used for DSC analysis. The melting curve showed two peaks, one at 139° C. and one at 147° C., with the higher peak being the larger. When the sample was cooled and reheated, a single melting peak at 135° C. was observed. Samples from the center of the rod had a density of 0.949 g/ml and a crystallinity index (IRCI) of 0.373. ASTM Type I tensile specimens were prepared form the rod, and the following test results were obtained:

| Modulus (kpsi) | 361 |
|---|---|
| Tensile Stress (yield, kpsi) | 3.96 |
| Tensile Stress (break, kpsi) | 5.53 |

Creep specimens in the form of 0.5" cubes were also prepared from the center of the rod. A creep of 1.2% was observed under 1000 psi load (ASTM F-648).

EXAMPLES 15–17

The procedure of Example 14 was employed in the subsequent examples, except that in Example 16 the Hoechst Hostalert GUR 415 UHMWPE rod dimensions were 3"×60". The enhancement temperature in each example was 250° C. Enhancement pressure and properties, determined as previously described, are given in the table below.

| Ex. | Press (MPa) | Modulus (kspi) | TS (Y) (kpsi) | TS (B) (kpsi) | Creep (%) | IRCI | Density (g/ml) |
|---|---|---|---|---|---|---|---|
| 15 | 255 | 405 | 4.12 | 5.53 | 0.97* | 0.401 | 0.951 |
| 16 | 255 | 364 | 3.98 | 5.30 |  | 0.410 | 0.951 |
| 17 | 269 | 424 | 4.12˙ | 5.56 | 0.95* | 0419 | 0.951 |

*ASTM F-648

The products of Examples 15–17 each display two peaks in their DSC meeting point curves.

EXAMPLE 18

A reactor as described in Example 4 was preheated to 220° C. and charged with a 3" diameter×18" rod of Hoechst Hostalen GUR 415 UHMWLPE, fabricated by Westlake, which had been preheated in an oven for 4 hours at 325° C. The closed vessel containing the preheated polymer was pressured with water to 2500 atm (253 MPa). While maintaining a pressure of 2500 atm (253 MPa), the vessel was cooled slowly to 185° C., held 2 h, then cooled slowly to 175° C., held for 2 h, then cooled slowly to 150° C., then rapidly to 80° C., after which the pressure was then released.

The product showed DSC melting endotherms at 140.8° C. and 150.0° C. (198.3 J/g). Upon remelting, a single peak remained at 135.2° C. (148.0 J/g). Tensile properties of samples cut from axial and transverse portions of the product rod-were determined:

| Tensile Properties (axial sample): | |
|---|---|
| Stress at yield, psi | 3923 |
| Stress at max, psi | 5635 |
| Stress at break, psi | 5635 |
| Modulus, kpsi | 265.9 |
| Elongation, % | |
| at yield, | 13.3 |
| at break | 502 |
| Tensile Properties (transverse sample): | |
| Stress at yield, psi | 4017 |
| Stress at max, psi | 6127 |
| Stress a break, psi | 6127 |
| Modulus, kpsi | 300.0 |
| Elongation, % | |
| at yield | 18 |
| at break | 455 |

EXAMPLE 19

The procedure of Example 14 was followed except that the reactor had an internal diameter of 4 inches and a length of about 18 inches. The reactor was charged with a 3 inch diameter×12⅝ inch cylinder (rod) of Hoechst Hostalen GUR 415 UHMWLPE fabricated by Westlake. The closed reactor was evacuated, filled with water, and heated to 220° C. The water developed a pressure of 3000 psi (20.7 MPa). Temperature was maintained at 220° C. for 2 hours to completely melt the polymer. Pressure in the reactor was then increased to 45,000 psi (310.5 MPa), and the reactor and its contents were allowed to cool slowly to 49° C. over a 5.5 hour period; cooling to 145° C. took approximately 2 hours.

The white product was machined first to a cylinder 4.59 cm high×3.57 cm diameter. A hole 1.29 cm in diameter was drilled along the axis of the cylinder. Then, using a lathe, 8 slots were cut from the outer circumference of the cylinder, 0.25 cm wide to a depth of 0.8 cm, providing 8 disks of polymer 0.28 cm thick attached to the central core of the cylinder (FIG. 2, sample 103). The test cylinder was then placed in a bath containing ethylene glycol (heat transfer medium, chemically and physically inert to polyethylene). The bath was slowly heated and held at a temperature of 128°–132° C. for 30 minutes, then cooled to room temperature. The test cylinder, including all disks, was unchanged in shape, dimensions and color.

COMPARATIVE EXAMPLE 1

Example 2 of U.S. Pat. No. 3,944,536 was followed in essential part. A cylinder 13/16 inch diameter×4 inches in length was cut from a 3 inch diameter cylinder of Hoechst Hostalen GUR 415 UHMW linear polyethylene, fabricated by Poly Hi. The smaller cylinder was place in a high pressure vessel having a 1⅜ inch diameter bore and fitted with a floating piston powered by hydraulic pressure. A liquid-tight seal on the piston prevented the hydraulic fluid, water, from contacting the polyethylene.

The vessel and its contents were heated at 170° C. for 2 hours. The hydraulic piston then applied 45,000 psi (310.5 MPa) pressure to the polyethylene and the vessel and contents were allowed to cool under this pressure. Cooling to 145° C. took 45 minutes. Pressure was released after 8.5 hours, when the temperature was 26° C.

A test cylinder was fabricated from the product precisely as described for the test cylinder in Example 19, and subjected to 30 minutes in an ethylene glycol bath at 128°–132° C., as described in Example 19. Both test cylinders were heated together in the same ethylene glycol bath. In contrast to the result in Example 19, the test cylinder was somewhat discolored and markedly misshapen; the disks in particular were substantially warped (cup-shaped) (FIG. 2, sample 15).

This example, together with Example 19, affords additional evidence that the pressure recrystallization process of U.S. Pat. No. 3,944,536 results in a different, dimensionally less stable product than that provided by Process 1 of the present invention. It is known that the results of the 130° C./30 min test correlate well with long-term dimensional stability under normal use conditions of UHMWLPE prosthetic devices. Poorer performance of UHMWLPE products of the prior art in such tests is believed to arise largely from inhomogeniety and the presence of internal stresses.

What is claimed is:

1. A process for preparing an improved folded chain ultrahigh molecular weight linear polyethylene having a molecular weight of at least 800,000 consisting essentially of the following steps:

(a) forming an article of an ultrahigh molecular weight linear polyethylene having a molecular weight of at least 800,000;

(b) subjecting said article to a temperature of 320°–345° C. in an inert atmosphere without the application of external pressure for at least 0.5 hour; and (c) cooling the article without the application of external pressure non-precipitously to a temperature of about 130° C. or below, the rate of cooling being such that temperature gradients in the article are substantially avoided.

2. The process of claim 1 wherein the temperature in step (b) is maintained for at least three hours.

3. A process in which the folded chain ultrahigh molecular weight polyethylene produced by the process of claim 1 having a molecular weight of at least 800,000, and exhibiting a flexural modulus of 150–300 kpsi, a tensile stress at yield of 3.5–4.3 kpsi, a tensile stress at break of 4–6 kpsi, a tensile modulus of 150–300 kpsi, a notched Izod impact resistance of 15–25 ft. lb per in. of notch, an elongation at break of 200–1400%, a creep at a compression of 1 kpsi of less than 2% after 24 hours at a temperature of 23° C. and a relative humidity of 50%; and an infrared crystallinity index of at least 0.35 is processed by the additional steps consisting essentially of:

(a) heating the article in a liquid that is inert to the polymer under process conditions to a temperature of 190°–300° C., until the article is molten, then raising the pressure of at least 280 MPa (b) cooling to about 160°–170° C. or lower while maintaining a pressure of at least 280 MPa, the rate of cooling being such that temperature gradients in the article are substantially avoided; and (c) cooling to a temperature below about 130° C. and reducing the pressure to about 100 kPa in a manner such that remelting the article is prevented.

4. The process of claim 1 wherein the inert atmosphere is a gaseous, vaporous or liquid environment wherein the gas vapor or liquid is selected from the group consisting of water, nitrogen, noble gases, a low melting metal alloy such as Wood's metal and perfluoroalkylpolyethers.

5. The process of claim 4 wherein the liquid is water.

6. The process of claim 1 wherein the article is a film or a prosthetic shape for replacement of joints in the human body.

7. The process of claim 1 wherein the article is heated in step (a) at 320° to 345° C. for at least 3 hours.

8. A process in which the folded chain ultrahigh molecular weight polyethylene produced by the process of claim 1 having a molecular weight of at least 800,000, and exhibiting a flexural modulus of 150–300 kpsi, a tensile stress at yield of 3.5–4.3 kpsi, a tensile stress at break of 4–6 kpsi, a tensile modulus of 150–300 kpsi, a notched Izod impact resistance of 15–25 ft. lb per in. of notch, an elongation at break of 200–1400%, a creep at a compression of 1 kpsi of less than 2% after 24 hours at a temperature of 23° C. and a relative humidity of 50%; and an infrared crystallinity index of at least 0.35 is processed by the additional steps consisting essentially of:

(a) heating the article in a liquid that is inert to the polymer under process conditions to a temperature of 190°–300° C., until the article is molten, then raising the pressure of between 230 MPa and less than 280 MPa (b) cooling to about 160°–170° C. or lower while maintaining a pressure of between 230 and less than 280 MPa, the rate of cooling being such that temperature gradients in the article are substantially avoided; and (c) cooling to a temperature below about 130° C. and reducing the pressure to about 100 kPa in a manner such that remelting the article is prevented.

9. The process of claim 8 wherein the surface of the article is shaved after step (c).

10. The process of claim 8 wherein the liquid is water.

11. The process of claim 8 wherein the temperature of step (a) is 200° to 300° C.

12. The process of claim 8 wherein the cooling rate in step (b) is no greater than 60° C. per hour.

13. The process of claim 8 wherein the cooling rate in step (b) is no more than 10° C. per hour.

* * * * *